United States Patent

Geuder

[11] Patent Number: 6,074,396
[45] Date of Patent: Jun. 13, 2000

[54] HOLLOW NEEDLE FOR AN OPHTHALMIC SURGICAL INSTRUMENT

[76] Inventor: Volker Geuder, Görrestrasse 67, Heidelberg, Germany

[21] Appl. No.: 09/056,458

[22] Filed: Apr. 7, 1998

[51] Int. Cl.[7] ........................................ A61F 9/00
[52] U.S. Cl. .............................. 606/107; 606/169; 604/22
[58] Field of Search ....................... 606/107, 169, 606/171, 128; 604/19, 22

[56] References Cited

U.S. PATENT DOCUMENTS

| 4,816,018 | 3/1989 | Parisi | 604/22 |
| 5,451,229 | 9/1995 | Geuder et al. | 606/107 |
| 5,464,389 | 11/1995 | Stahl | 604/22 |

FOREIGN PATENT DOCUMENTS

4313245C2  10/1994  Germany .

*Primary Examiner*—Michael Buiz
*Assistant Examiner*—Jennifer Maynard
*Attorney, Agent, or Firm*—Collard & Roe, P.C

[57] ABSTRACT

A hollow needle for use as an ultrasonic probe for crushing lenses during ophthalmic surgery. The needle has a suction channel extending toward the distal end into a radially expanding segment. The segment having a plurality of coaxial bores having stepped diameters forming ring shoulders. The bores extend from the distal end into the hollow needle. A plurality of tetrahedrally-shaped cuts are arranged around the circumference of at least one of the ring shoulders or the distal end of the needle. The cuts substantially enlarge the reflecting surface area for the ultrasonic waves and thereby permit intensive admission of ultrasound to the operative tissue. The ring shoulders may be additionally or alternatively be undercut for obtaining additional reflecting surfaces.

12 Claims, 2 Drawing Sheets

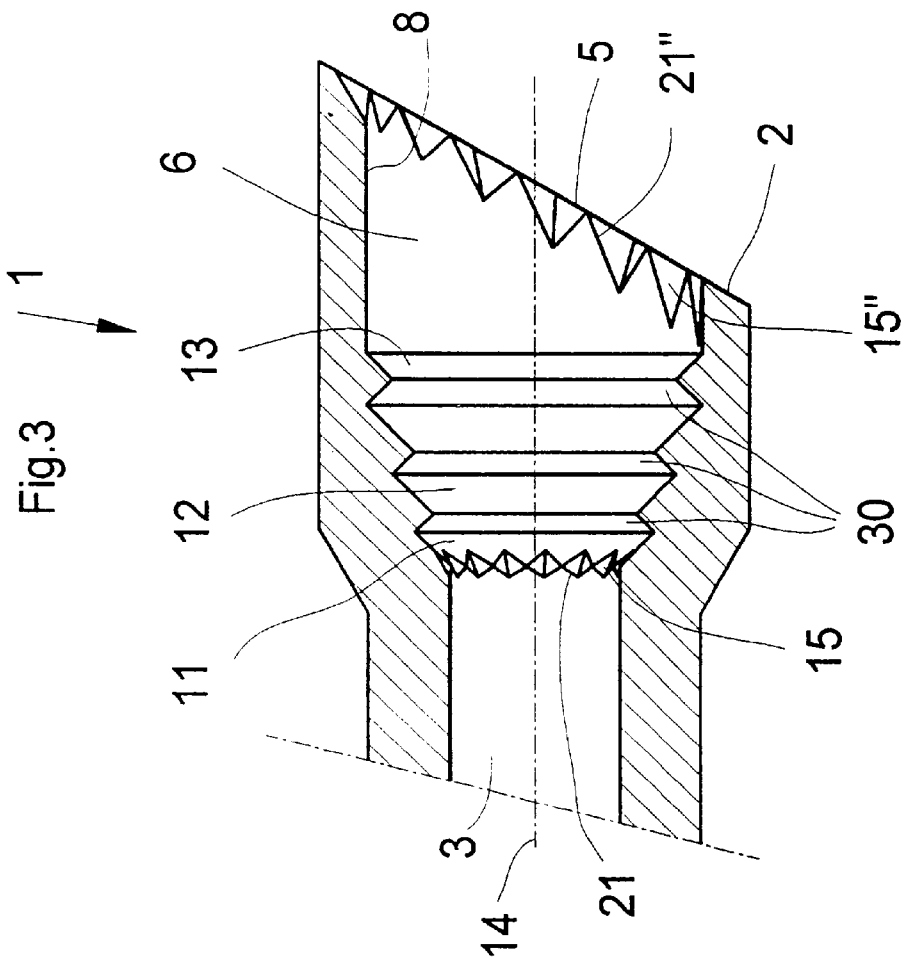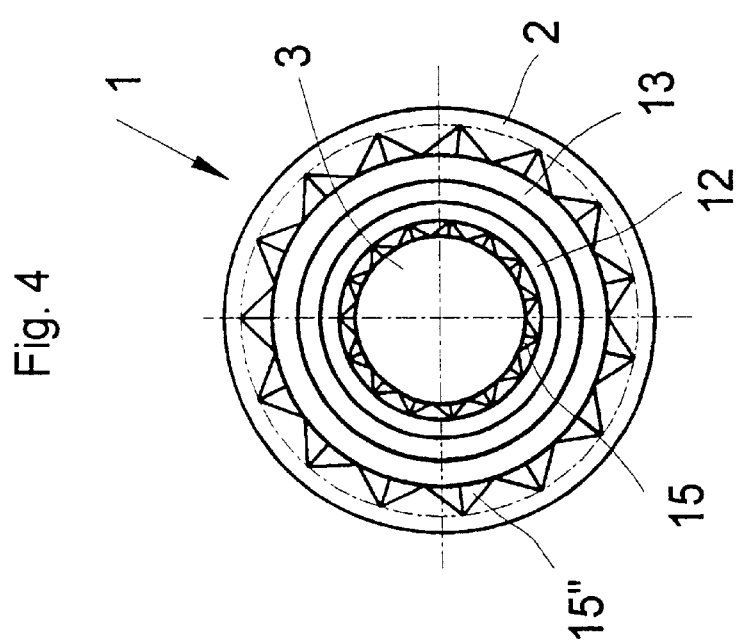

HOLLOW NEEDLE FOR AN OPHTHALMIC SURGICAL INSTRUMENT

BACKGROUND OF THE INVENTION

1. Field of the Invention

The present invention relates to a hollow needle for an ophthalmic surgical instrument that crushes lenses by actuating the hollow needle at high frequency, and removes lens debris by suction. The hollow needle has a suction channel and a segment radially expanding toward a ring-shaped distal end of the hollow needle. The channel consists of bores extending coaxially with the suction channel from the distal end into the hollow needle, and has stepped diameters connected by conical ring shoulders.

2. The Prior Art

It is known that cataract operations are successfully performed in the field of the ophthalmic surgery using hollow needles actuated by ultrasound. In such operation, the hollow needle, which is axially movable at high frequency, is guided directly up against the cataract. The ultrasonic waves emitted from the ring-shaped distal end of the needle lead to emulsification of the tissue. The separated lens pieces are then removed by suction through the hollow needle together with the rinsing liquid previously admitted to the eye.

In order to facilitate the removal of old cataracts, where the lens tissue is very hard, additional measures have been implemented in order to intensify or focus the ultrasonic field emitted from the needle point. A hollow needle of this type is known, for example from German Patent 43 13 245 A 1. The suction channel in this needle has a segment extending radially in the direction of the point of the needle. This segment consists of three stepped bores extending coaxially with each other from the distal end of the hollow needle into the needle, so that the cross section of the suction channel widens step by step in the direction of the aperture of the point of the needle. The ring or annular shoulders extending between the bores serve as additional surfaces for reflecting the ultrasonic waves, which results in an intensified ultrasonic field in front of the point of the needle. Additional focusing of the emitted ultrasonic waves is accomplished by providing the ring shoulders with a conical shape.

The known hollow needle has been successfully employed in the majority of cases. However, with cataracts having particularly hard lens tissue, the ultrasonic field emitted by the hollow needle may not suffice for emulsifying the lens tissue completely. Larger pieces of the lens tissue are crushed further on the annular shoulders, which may cause clogging of the suction channel.

SUMMARY OF THE INVENTION

Therefore, it is an object of the present invention to improve a hollow needle of the above-specified type having an enlarged surface area for reflecting ultrasonic waves for intensifying the emitted ultrasonic field.

This object is accomplished by hollow needle having cuts arranged on at least one ring shoulder and/or widening towards the distal end. The cuts have side surfaces inclined towards the surface of the ring shoulder or distal end.

These cuts distinctly enlarge the ultrasonic wave-reflecting surface area as compared to the known design without requiring any enlargement of the diameter of the needle at the distal end. Ultrasonic waves emitted from the side surfaces of the cuts as well as the ring shoulder and/or the distal end are superimposed on each other in a defined zone in front of the cut. A piece of lens tissue to be crushed is consequently acted upon by ultrasound multiple times and from various directions, which causes extensive emulsification even with hard pieces of lens tissue.

The cuts preferably extend substantially radially relative to the longitudinal axis of the suction channel and are arranged with equal angular spacings around the circumference of the ring shoulder or distal end, which results in uniform admission of ultrasound.

The cuts are usefully arranged on the dividing line between the ring shoulder and the bore radially bordering on the inside of the ring shoulder. The cuts form notches with two triangular side surfaces inclined against each other, and consequently have the geometry of a tetrahedron. The cuts must not absolutely cover the entire radial expanse of the ring shoulder or distal end. The ultrasonic waves coming from the two side surfaces consequently travel not only in the direction of the axis of the front segment of the suction channel but also in additional directions, and are therefore additionally focused with respect to each other.

At least one of the two cutouts associated with each tetrahedral notch preferably has the cross section of a triangle with equal legs and a base extending tangentially relative to the respective bore. With notches arranged in the ring shoulders, both cutouts are preferably shaped with equal legs. This ensures that the ultrasonic waves emitted from the two side surfaces have the same intensity in the zone of the superimposition. If the hollow needle has a beveled distal end, only the cutouts arranged radially with respect to the suction channel have equal legs, whereas the others are shaped to conform with the bevel in such a way that no eccentric displacement or shifting of the ultrasonic field will occur within the zone ahead of the front end of the hollow needle.

In another advantageous embodiment, the dividing line between the ring shoulders or distal end and the respective bore is completely covered with tetrahedral notches and forms a substantially serrated boundary between the ring shoulders and the wall of the bore. This results in particularly intense reflection of ultrasonic waves within the zone of the respective ring shoulder.

The side surfaces of the tetrahedral notches of at least one ring shoulder or the distal end are inclined against each other in an approximately right-angled manner, preferably with an angle of about 85° to about 95°. In this way, superimposition of the two ultrasonic waves coming from the side surfaces of tetrahedral notches takes place within the immediate proximity of the respective ring shoulder. Lens debris separated from the cataract and flowing into the suction channel is therefore acted upon by a particularly strong ultrasonic field, especially if this debris becomes caught on one of the ring shoulders. This device also reliably prevents clogging of the hollow needle by large pieces of lens tissue.

Preferably, all ring shoulders of the hollow needle and the front end have cuts. In this embodiment, pieces of lens tissue are detached by an ultrasonic field that is intensified by the cuts, and sucked into the suction aperture. The pieces of tissue are acted upon further by strong ultrasonic waves within the area of each ring shoulder and are reliably crushed so that they can be flawlessly discharged by the suction channel.

So as to simplify the manufacture of the hollow needle, the distal end and the ring shoulders each have the same amount of cuts and the cuts of different ring shoulders are arranged along planes extending radially relative to the suction channel.

It is particularly advantageous if the ring shoulders having the cuts have a conical shape. This design focuses the remaining ultrasonic field that is not reflected by the side surfaces of the cuts and achieves powerful admission of ultrasound across the entire cross section of the hollow needle.

Furthermore, an additional reflecting surface is formed by suitably undercutting at least one ring shoulder. This creates an additional reflecting surface for the ultrasonic wave developed in the interior of the hollow needle. As explained above, the ultrasonic wave is generated by axially moving the hollow needle back and forth at high frequency. Due to the fact that a reflecting surface is now available facing the direction of suction, the ultrasonic wave is also reflected in the direction of suction. Consequently, a longitudinally reciprocating ultrasonic wave is produced in the interior of the hollow needle.

This additional reflection of the ultrasonic wave in the direction of suction crushes the lens pieces already sucked into the interior of the hollow needle even more rapidly and more effectively. The lens pieces are thus acted upon by ultrasonic waves both in the direction of the surgery and in the direction of suction, i.e., on both sides. The lens pieces are, consequently, crushed from two sides instead of only from one side and are therefore cut up almost twice as fast. This way, further transport through the hollow needle can take place smoothly.

According to an additional embodiment, the ring shoulders are equipped with both tetrahedral cuts and an additional reflecting surface formed by undercutting.

Particularly good focusing of the ultrasonic wave in both the direction of surgery and the direction of suction is obtained if the surface of the ring shoulder that is open in the direction of surgery and the reflecting surface additionally formed by the undercut jointly form an angle of about 90°.

The additional reflecting surface can be simply produced a cutting tool for inside cutting, which must be introduced into the hollow needle.

BRIEF DESCRIPTION OF THE DRAWINGS

The invention is described in greater detail in the following two exemplified embodiments. The following is schematically shown in the drawing, wherein similar numerals designate similar elements throughout several views.

FIG. 3 shows a partial longitudinal section through another hollow needle with additional reflecting surfaces; and FIG. 4 shows a face view of the hollow needle according to FIG. 3.

DETAILED DESCRIPTION OF PREFERRED EMBODIMENTS

Figure 1:
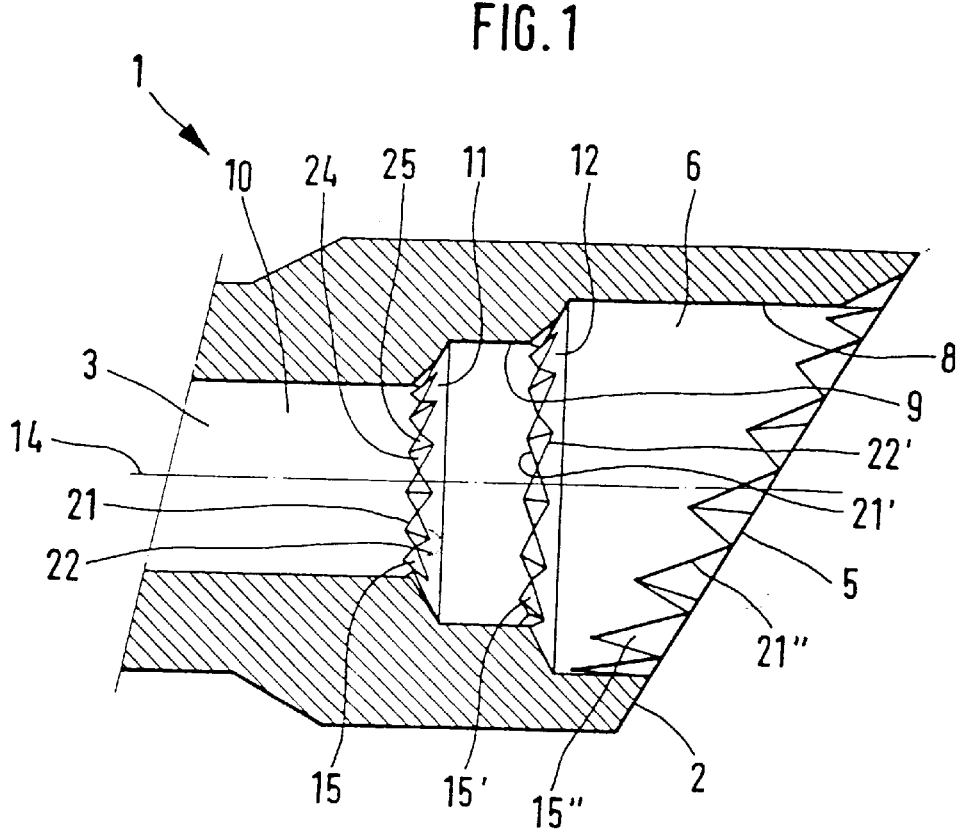
FIG. 1 shows a partial longitudinal section of the front segment of the hollow needle.

Turning now in detail to the drawings, and in detail to FIG. 1, there is shown the front segment of a hollow needle 1, that is part of an ophthalmic surgical instrument for ultrasonically removing cataracts. Hollow needle 1 is put into high-frequency axial motion by an ultrasonic generator (not shown), which causes reflection of an ultrasonic field on distal end 2 of hollow needle 1. When employed as intended, the instrument is inserted with distal end 2 through an incision on the edge of the cornea of an eye and into the anterior chamber of the eye, and placed on the lens to be crushed. The lens is emulsified by the administering of ultrasound emitted from distal end 2, and the separated pieces of lens are discharged through suction channel 3 extending through the inside of hollow needle 1. To permit targeted application of hollow needle 1 within a predetermined section of tissue, distal end 2 of hollow needle 1 has a bevel 5 which is angled at approximately 30°.

Segment 6 of suction channel 3, which borders on distal end 2, is radially expanded step by step towards distal end 2 by two coaxial bores 8, 9 having different diameters. Outer bore 8 has a larger diameter than the inner bore 9. The two bores 8, 9 are separated from each other as well as from the rear segment 10 of suction channel 3 by ring shoulders 11, 12. Ring shoulders 11 and 12 are conically shaped and have an angle of inclination of about 60° relative to the longitudinal axis 14 of suction channel 3.

Cuts 15, 15', 15" are arranged in the manner described below in the two ring shoulders 11, 12, as well as in distal end 2 of hollow needle 1. All cuts 15, 15', 15" are shaped in the same way. Therefore, only one cut 15 on dividing line 18 between the rear segment 10 of suction channel 3 and the inner ring shoulder 11 is described in greater detail.

At dividing line 18, where the rear segment of suction channel 3 changes into the inner ring shoulder 11, the rear segment 10 and the inner ring shoulder 11 have prism-shaped cuts 15 comprising triangular cutouts 21, 22 with the edges of said cutouts being connected by two triangular limiting surfaces 24, 25. The cutouts 21 of the rear segment 10 and the cutouts 22 of the inner ring shoulder 11 as well as the limiting surfaces 24, 25 thus represent the surfaces of a tetrahedron.

As mentioned above, cuts 15', 15" of the outer ring shoulder 12 and of distal end 2 are formed correspondingly. While the triangular cutouts 21, 22, 21', 22' of the two ring shoulders 11, 12 each have a cross section with equal legs, the cutouts 21" in the wall of the outer bore 8 are shaped skewed such that in spite of bevel 5, there will be no eccentric shifting of the ultrasonic field reflected from distal end 2.

The two ring shoulders 11, 12 as well as distal end 2 each have the same number of cuts 15, 15', 15". The cuts are arranged along planes extending radially through the longitudinal axis 14 of suction channel 3.

Limiting surfaces 24, 25 of cuts 15, 15', 15" are disposed at approximately right angles relative to each other. In this way, the maximum intensity of the ultrasonic field generated in the needle is disposed within the immediate proximity of dividing lines 18, 18', 18".

When employed as intended, distal end 2 of the hollow needle is guided against the cataract. The strong ultrasound emitted from limiting surfaces 24, 25 of cuts 15, 15', 15" causes pieces of tissue to be detached from the cataract and discharged via suction channel 3. Pieces of lens tissue remaining stuck on ring shoulders 11, 12 in this process are again acted upon by a powerful ultrasonic field within the immediate zone of transition of ring shoulders 11, 12. The ultrasonic field is emitted from the limiting surfaces of the corresponding cuts 15, 15'. Particles are detached in this way, particularly parts of the lens tissue remaining caught, for example on ring shoulder 11 or 12, until the piece of lens tissue has a particle size sufficiently small to be discharged through suction channel 3.

Figure 2:
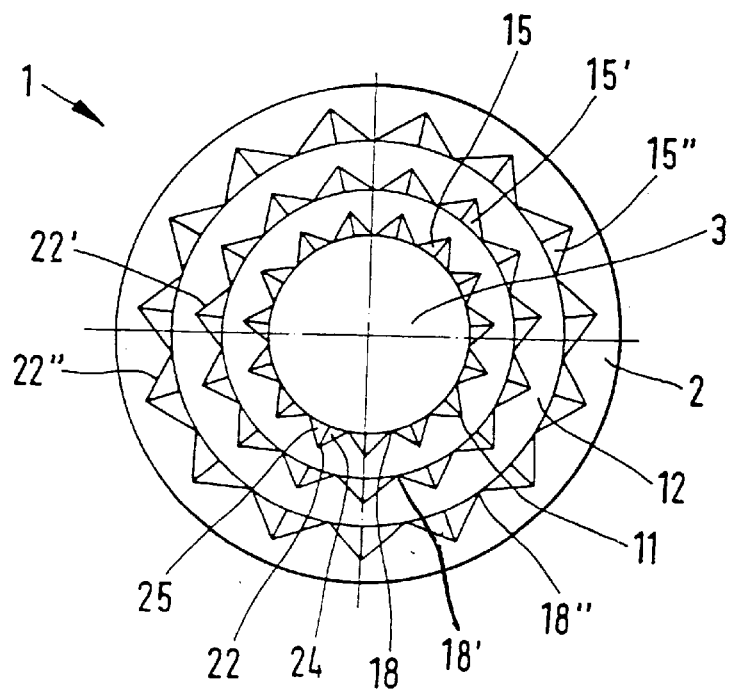
FIG. 2 shows a face side view of the hollow needle according to FIG. 1.

The hollow needle shown in FIGS. 3 and 4 represents the most preferred embodiment of the invention described above. The reference numerals assigned to analogous features are the same as the ones used with the hollow needle shown in FIGS. 1 and 2. The hollow needle shown in FIGS. 3 and 4 differs from the hollow needle shown in FIGS. 1 and 2 only in that there is a ring shoulder 13 in addition to ring shoulders 11 and 12. Furthermore, all ring shoulders are additionally provided with an additional reflecting surface 30, which faces in the direction of suction. Reflecting surface 30 has been cut from the hollow needle by undercutting the respective ring shoulders 11, 12, 13 with an inside cutting or turning tool. In the present embodiment, only ring shoulder 13, which is disposed immediately adjacent to suction channel 3, and distal end 2 of hollow needle 1 are provided with corresponding cuts 15 and, respectively 15".

In addition to the reflecting surfaces additionally obtained for the ultrasonic wave through the ring shoulders 11, 12 and 13 as well as cuts 15, 15", the additional reflecting surface 30 supplies yet another reflecting surface for the ultrasonic wave generated by the longitudinal high-frequency motion of the needle 1. As opposed to surfaces 11, 12, 13, 15 and 15', the additional reflecting surfaces 30 reflect the ultrasonic wave in the direction of suction. The ultrasonic wave generated in the interior of the hollow needle consequently travels back and forth between the direction of the surgical intervention and the direction of the suction. This causes crushing the lens pieces sucked into the interior of the hollow needle on both sides. This crushing of the lens pieces on both sides permits rapid and more efficient crushing of the lens pieces and thus more rapid removal of the pieces by suction. This means that the surgery can be carried out faster and with fewer complications.

Particularly good focusing of the ultrasonic wave on the interior of the hollow needle is achieved if both ring shoulders 11, 12, 13 and the additional reflecting surfaces 30 have an angle of inclination of about 60° relative to the longitudinal axis 14 of suction channel 3. In this case, the surface of ring shoulders 11, 12 and 13 and the additional reflecting surfaces 30 produced by the undercutting thus together form an angle of at least approximately 90°.

Accordingly, while only a few embodiments of the present invention have been shown and described, it is obvious that many changes and modifications may be made thereunto without departing from the spirit and scope of the invention as defined in the appended claims.

What is claimed is:

1. An ophthalmic surgical instrument for high frequency lens crushing and removing the lens debris by suction, comprising:
    a hollow needle having a ring-shaped distal end:
    a suction channel extending through said hollow needle and having a longitudinal axis; and
    a segment radially expanding toward said ring-shaped distal end and comprising:
        a plurality of bores arranged coaxially with said suction channel and extending from the distal end into the suction channel, said bores having walls with stepped diameters separated by ring shoulders; and
        a plurality of cuts formed on at least one of the distal end and ring shoulders, said cuts expanding toward said at least one of said distal end and ring shoulders, and having side surfaces inclined relative to said at least one of said distal end and ring shoulders.

2. The instrument according to claim 1, wherein the cuts expand substantially radially relative to the longitudinal axis of the needle and are arranged circumferentially around said at least one of said distal end and ring shoulders with equal spacing from one another.

3. The instrument according to claim 2, wherein each cut has the shape of a substantially tetrahedral notch formed by two substantially triangular side surfaces, said side surfaces extending between a first substantially triangular cutout opening toward the longitudinal axis of the suction channel and disposed on one of said distal end and ring shoulders, and a second substantially triangular cutout arranged on an adjacent bore and opening toward said one of said distal end and ring shoulders.

4. The instrument according to claim 3, wherein at least one of the cutouts has a triangular cross section with legs of equal length and a base extending tangentially relative to said adjacent bore.

5. The instrument according to claim 3, wherein each second substantially triangular cutout touches an adjacent second substantially triangular cutout in the circumferential direction around said one of said distal end and ring shoulders and forms substantially serrated limitations between one of said distal end and ring shoulders and the wall of said adjacent bore.

6. The instrument according to claim 3, wherein the two side surfaces of each substantially tetrahedral notch are inclined against each other and form an angle of from about 85° to about 95°.

7. The instrument according to claim 1, wherein said cuts are formed on said distal end and all of said ring shoulders.

8. The instrument according to claim 7, wherein the distal end and ring shoulders each have the same number of cuts and wherein said cuts are arranged in planes extending radially relative to said suction channel.

9. The instrument according to claim 1, wherein the ring shoulders are conically shaped.

10. An ophthalmic instrument for high frequency lens crushing and removal of lens debris by suction, comprising
    a hollow needle having a ring-shaped distal end;
    a suction channel extending through said hollow needle; and
    a segment radially expanding toward said distal end and comprising a plurality of bores extending coaxially with the suction channel from the distal end into the hollow needle and having stepped diameters separated by ring shoulders, wherein at least one ring shoulder is undercut to form a reflecting surface facing away from said distal end.

11. An ophthalmic surgical instrument for high frequency lens crushing and removal of the lens debris by suction, comprising:
    a hollow needle having a ring-shaped distal end;
    a suction channel extending through said hollow needle; and
    a segment radially expanding toward said ring-shaped distal end and comprising:
        a plurality of bores arranged coaxially with each other and said suction channel and extending from the distal end into the suction channel, said bores having stepped diameters separated by ring shoulders; and
        a plurality of cuts formed on at least one of the distal end and ring shoulders, said cuts having shapes expanding toward said at least one of said distal end and ring shoulders, and having side surfaces inclined relative to said at least one of said distal end and ring shoulders;
    wherein at least one ring shoulder is undercut to form a reflecting surface facing away from the distal end.

12. The instrument according to claim 10, wherein the additional reflecting surface and said at least one ring shoulder enclose an angle of at least about 90°.

* * * * *